United States Patent
Kozak et al.

(10) Patent No.: US 8,353,858 B2
(45) Date of Patent: Jan. 15, 2013

(54) RAPID EXCHANGE FLUID JET CATHETER AND METHOD

(75) Inventors: Debra M. Kozak, Forest Lake, MN (US); Michael J. Bonnette, Minneapolis, MN (US); Eric J. Thor, Arden Hills, MN (US); David B. Morris, Anoka, MN (US); John L. Teschendorf, Lino Lakes, MN (US); Douglas J. Ball, Blaine, MN (US); Stephen E. Weisel, Brook Park, MN (US); Michael Schrom, Wyoming Township, MN (US)

(73) Assignee: Medrad, Inc., Indianola, PA (US)

( * ) Notice: Subject to any disclaimer, the term of this patent is extended or adjusted under 35 U.S.C. 154(b) by 276 days.

(21) Appl. No.: 12/793,121

(22) Filed: Jun. 3, 2010

(65) Prior Publication Data

US 2010/0312223 A1      Dec. 9, 2010

Related U.S. Application Data

(60) Provisional application No. 61/183,642, filed on Jun. 3, 2009.

(51) Int. Cl.
*A61N 1/30* (2006.01)

(52) U.S. Cl. ......................................................... 604/19
(58) Field of Classification Search .................... 604/19, 604/43, 523–527, 22, 35, 264, 118–120, 604/103.04; 606/127–128, 192–194
See application file for complete search history.

(56) References Cited

U.S. PATENT DOCUMENTS

| | | | |
|---|---|---|---|
| 5,490,837 A * | 2/1996 | Blaeser et al. | 604/103.11 |
| 6,755,803 B1 | 6/2004 | Le et al. | |
| 6,805,684 B2 | 10/2004 | Bonnette et al. | |
| 6,875,193 B1 * | 4/2005 | Bonnette et al. | 604/22 |
| 7,842,010 B2 | 11/2010 | Bonnette et al. | |
| 7,879,022 B2 | 2/2011 | Bonnette et al. | |
| 8,012,117 B2 | 9/2011 | Bonnette et al. | |

* cited by examiner

*Primary Examiner* — Christopher D Koharski
(74) *Attorney, Agent, or Firm* — David Schramm (57) ABSTRACT

Catheters including guidewire tubes having a limited length and methods of using the catheters are described. The catheters may be delivered over guidewires in procedures that are commonly referred to as rapid-exchange delivery. In some embodiments, the catheters may be miniature flexible thrombectomy catheters that may be used to remove thrombus or other unwanted material from a body blood vessel or other small regions of body cavities in which the distal portion of the catheter has smaller external dimensions than the larger proximal portion.

15 Claims, 7 Drawing Sheets

RAPID EXCHANGE FLUID JET CATHETER AND METHOD

RELATED APPLICATION

The present application claims the benefit under 35 U.S.C. §119(e) of U.S. Provisional Patent Application No. 61/183,642, filed on Jun. 3, 2009 and titled RAPID EXCHANGE FLUID JET CATHETER AND METHOD, which is hereby incorporated by reference in its entirety.

Rapid exchange catheters including guidewire tubes and methods of using the same are described herein.

Catheters may be used for a variety of procedures. Some catheters, typically referred to as thrombectomy catheters, may be used to perform procedures in which thrombotic material is removed from a blood vessel (or other body lumen). The removed material may preferably be removed from the body through the thrombectomy catheter.

Examples of some thrombectomy catheters are described in, e.g., U.S. Patent Application Publication US 2008/0188831 A1, titled MINIATURE FLEXIBLE THROMBECTOMY CATHETER (Bonnette et al.); U.S. Pat. No. 6,875,193 (Bonnette et al.); U.S. Pat. No. 6,805,684 (Bonnette et al.); U.S. Pat. No. 6,755,803 (Le et al.); U.S. Patent Application Publication US 2006/0064123 A1 (Bonnette et al.); U.S. Patent Application Publication No. US 2007/0129679 (Bonnette et al.); etc.

SUMMARY

Catheters including guidewire tubes having a limited length and methods of using the catheters are described herein. The catheters may be delivered over guidewires in procedures that are commonly referred to as rapid-exchange delivery. In some embodiments, the catheters may be miniature flexible thrombectomy catheters that may be used to remove thrombus or other unwanted material from a body blood vessel or other small regions of body cavities in which the distal portion of the catheter has smaller external dimensions than the larger proximal portion.

The guidewire tubes used in the catheters described herein preferably terminate at locations that are located proximally from the distal ends of the catheters. The guidewire tubes may preferably terminate at a distal end that is located proximally from a fluid jet emanator that is provided within an exhaust lumen of the catheter.

In some embodiments, the catheters may include a distal body section that has a smaller cross-sectional size than a proximal body section to which the distal body section is attached. An exhaust lumen provided in the catheter to remove fluid delivered through the fluid jet emanator may also have a smaller cross-sectional area in the smaller distal body section than in the larger proximal body section. It may be preferred that the distal end of the guidewire tube terminate within the portion of the exhaust lumen located in the proximal body section such that the guidewire tube does not constrict the size of the exhaust lumen in the smaller distal body section of the catheter. In some embodiments, however, beneficial results can be achieved if the guidewire tube extends into the exhaust lumen of the distal body section, but terminates at or proximal to the fluid jet emanator contained within the distal catheter body section.

In some embodiments, the guidewire tube may be fixed within the catheter such that it remains in place throughout use of the catheter. In other embodiments, the guidewire tube may be removed from the catheter after having accomplished the function of guiding a guidewire through the catheter during advancement of the catheter to a selected internal body location.

In one aspect, the catheters described herein may include an elongated catheter body having a proximal end and a distal end, wherein a longitudinal axis extends between the proximal end and the distal end, and wherein the catheter body includes a proximal body section and a distal body section, wherein a distal end of the proximal body section is attached to a proximal end of the distal body section at a transition section of the catheter body; an exhaust lumen located within the catheter body, the exhaust lumen being aligned with the longitudinal axis, wherein the exhaust lumen has a proximal cross-sectional area on a proximal side of the transition section that is larger than a distal cross-sectional area of the exhaust lumen on a distal side of the transition section; a fluid jet emanator located in the distal body section; a fluid delivery tube attached to the fluid jet emanator, the fluid delivery tube extending through at least a portion of the proximal body section, wherein the fluid delivery tube passes from the proximal body into the distal body section through the transition section; and a guidewire tube located within only a portion of the catheter body, wherein the guidewire tube has a proximal end and a distal end, wherein the guidewire tube comprises a guidewire lumen extending from a proximal port at the proximal end of the guidewire tube to a distal port at the distal end of the guidewire tube, and wherein the distal port of the guidewire lumen opens into the exhaust lumen at a location proximal from the fluid jet emanator.

In some embodiments, the distal end of the guidewire tube is located between the proximal end of the distal body section and the proximal end of the guidewire tube.

In some embodiments, the proximal end of the guidewire tube is located in the proximal body section of the catheter body and the distal end of the guidewire tube is located between the proximal end of the distal body section and the proximal end of the guidewire tube.

In some embodiments, the proximal end of the guidewire tube is located in the proximal body section of the catheter body.

In some embodiments, the proximal end of the guidewire tube is located in the proximal body section of the catheter body and the distal end of the guidewire tube is located in the transition section.

In some embodiments, the catheters described herein may include one or more protrusions extending into the exhaust lumen in a direction transverse to the longitudinal axis.

In some embodiments, the distal end of the guidewire lumen is flared such that the distal port of the guidewire lumen is enlarged in a direction transverse to the longitudinal axis.

In some embodiments, the fluid jet emanator includes a guidewire orifice, such that a guidewire directed into the exhaust lumen from the distal end of the catheter body and advanced proximally toward the proximal end of the catheter body passes through the guidewire orifice before entering the distal port of the guidewire lumen.

In some embodiments, the catheter body includes a guidewire tube port that includes a seal, wherein the guidewire tube extends through the seal of the guidewire tube port and into the exhaust lumen, and wherein the seal restricts fluid flow out of the exhaust lumen through the guidewire port around the guidewire tube.

In some embodiments in which the catheter body includes a guidewire tube port that includes a seal, with the guidewire tube extending through the seal of the guidewire tube port and into the exhaust lumen, wherein the seal includes a seal orifice that seals around a guidewire extending through the guidewire tube port in the absence of the guidewire tube in the guidewire tube port.

In some embodiments in which the catheter body includes a guidewire tube port that includes a seal, with the guidewire tube extending through the seal of the guidewire tube port and into the exhaust lumen, the guidewire tube is removable from the guidewire tube port and the seal includes a seal orifice that seals around a guidewire extending through the guidewire tube port after removal of the guidewire tube from the guidewire tube port.

In some embodiments in which the catheter body includes a guidewire tube port that includes a seal, with the guidewire tube extending through the seal of the guidewire tube port and into the exhaust lumen, the fluid jet emanator includes a guidewire orifice, such that a guidewire directed into the exhaust lumen from the distal end of the catheter body and advanced proximally toward the proximal end of the catheter body passes through the guidewire orifice before entering the distal port of the guidewire lumen.

In some embodiments in which the catheter body includes a guidewire tube port that includes a seal, with the guidewire tube extending through the seal of the guidewire tube port and into the exhaust lumen, the distal end of the guidewire tube is located between the proximal end of the distal body section and the fluid jet emanator.

In some embodiments in which the catheter body includes a guidewire tube port that includes a seal, with the guidewire tube extending through the seal of the guidewire tube port and into the exhaust lumen, the proximal end of the guidewire tube is located in the proximal body section of the catheter body.

In some embodiments in which the catheter body includes a guidewire tube port that includes a seal, with the guidewire tube extending through the seal of the guidewire tube port and into the exhaust lumen, the proximal end of the guidewire tube is located in the proximal body section of the catheter body and wherein the distal end of the guidewire tube is located in the transition section.

In some embodiments in which the catheter body includes a guidewire tube port that includes a seal, with the guidewire tube extending through the seal of the guidewire tube port and into the exhaust lumen, the catheter may include one or more protrusions extending into the exhaust lumen in a direction transverse to the longitudinal axis.

In some embodiments in which the catheter body includes a guidewire tube port that includes a seal, with the guidewire tube extending through the seal of the guidewire tube port and into the exhaust lumen, the distal end of the guidewire lumen is flared such that the distal port of the guidewire lumen is enlarged in a direction transverse to the longitudinal axis.

In some embodiments of the catheters described herein, the catheter body includes an outflow orifice and an inflow orifice, wherein at least a portion of pressurized fluid delivered to the fluid jet emanator through the fluid delivery tube emanates from the catheter body through the outflow orifice, and wherein at least a portion of the fluid that emanates from the catheter body through the outflow orifice re-enters the catheter body through the inflow orifice, and further wherein the inflow orifice is located in the distal body section of the catheter body. In some embodiments, both the outflow orifice and the inflow orifice are located in the distal body section of the catheter.

In another aspect, the methods described herein may include a method of threading a guidewire into a catheter by inserting a proximal end of a guidewire into an exhaust lumen located proximate a distal end of a catheter; advancing the proximal end of the guidewire towards a proximal end of the catheter, wherein the guidewire advances through a guidewire orifice in a fluid emanator before entering a distal port of a guidewire lumen located within the exhaust lumen of the catheter; and advancing the proximal end of the guidewire through the guidewire lumen, wherein the proximal end of the guidewire exits the guidewire tube and the catheter through a proximal port of the guidewire lumen.

In some methods described herein, the guidewire tube occupies only a portion of the length of the catheter.

In some methods described herein, the catheter body includes a guidewire tube port that includes a seal, wherein the guidewire tube extends through the seal of the guidewire tube port and into the exhaust lumen, and the method includes removing the guidewire tube from the catheter after the proximal end of the guidewire exits the guidewire tube and the catheter through the proximal port of the guidewire lumen. In some methods, the seal includes a seal orifice that seals around the guidewire after the guidewire tube has been removed from the guidewire tube port.

In some methods described herein, the catheter includes an elongated catheter body having a proximal end and a distal end, wherein a longitudinal axis extends between the proximal end and the distal end, and wherein the catheter body includes a proximal body section and a distal body section, wherein a distal end of the proximal body section is attached to a proximal end of the distal body section at a transition section of the catheter body; and wherein the exhaust lumen is located within the catheter body, the exhaust lumen being aligned with the longitudinal axis, wherein the exhaust lumen has a proximal cross-sectional area on a proximal side of the transition section that is larger than a distal cross-sectional area of the exhaust lumen on a distal side of the transition section. In further embodiments, the catheter includes a fluid jet emanator located in the distal body section and a fluid delivery tube attached to the fluid jet emanator, the fluid delivery tube extending through at least a portion of the proximal body section, wherein the fluid delivery tube passes from the proximal body into the distal body section through the transition section.

The words "preferred" and "preferably" refer to embodiments of the catheters and methods described herein that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a seal may refer one seal or more than one seal unless explicitly limited to, e.g., "only one seal."

The term "and/or" means one or all of the listed elements or a combination of any two or more of the listed elements.

The above summary is not intended to describe each embodiment or every implementation of the present disclosure. Rather, a more complete understanding of the devices set forth in this disclosure will become apparent and appreciated by reference to the following Detailed Description of Exemplary Embodiments and claims in view of the accompanying figures of the drawings.

DETAILED DESCRIPTION OF EXEMPLARY EMBODIMENTS

In the following detailed description of exemplary embodiments, reference is made to the accompanying figures of the drawing which form a part hereof, and in which are shown, by way of illustration, specific embodiments of the catheters and methods. It is to be understood that other embodiments may be utilized and structural changes may be made without departing from the scope of the present disclosure.

Figure 1:
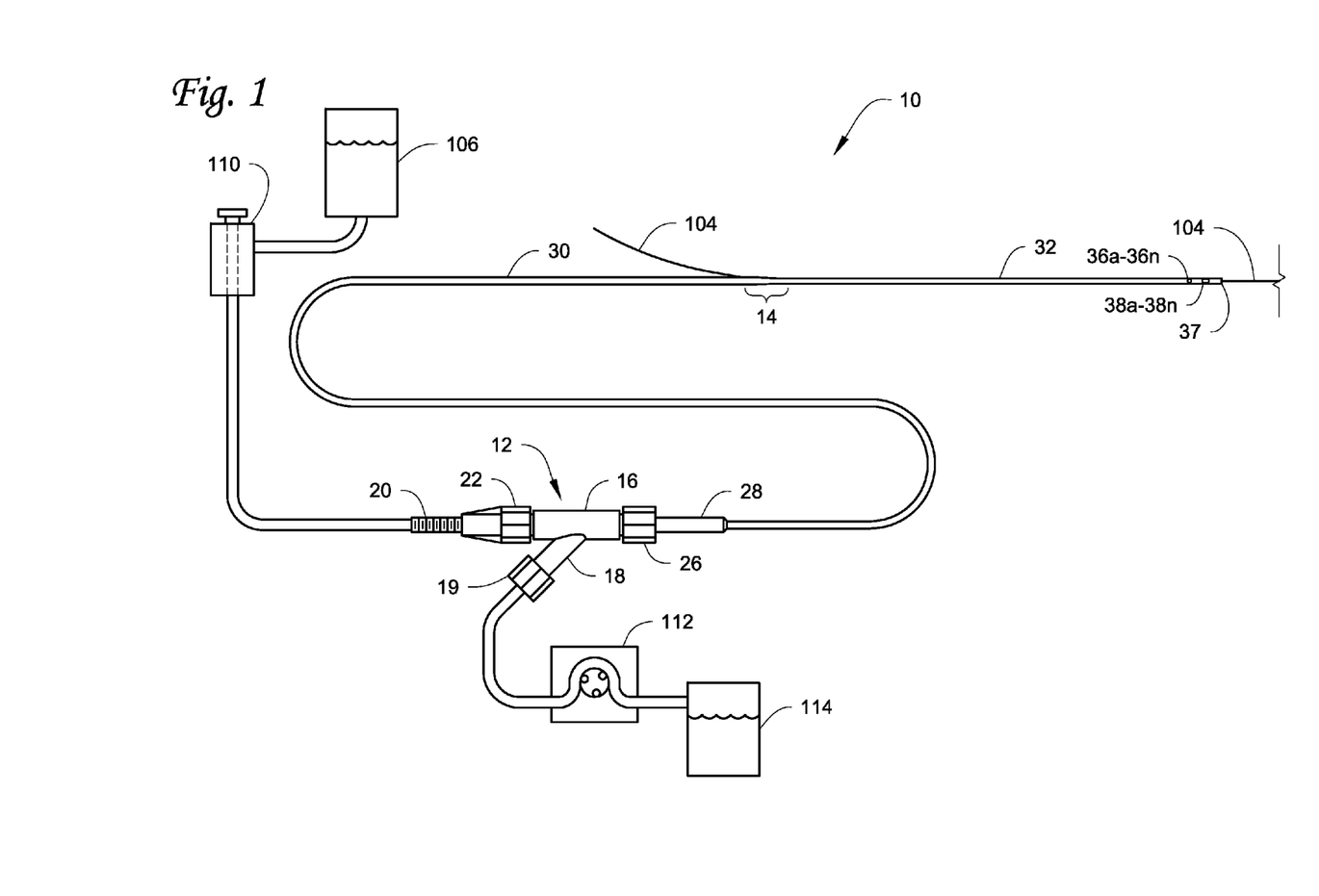
FIG. 1 depicts an exemplary embodiment of a system including an exemplary embodiment of a catheter as described herein.

FIG. 1 is a plan view that depicts a variety of components that may be provided in a system that includes a catheter 10 as described herein. Embodiments of many of these components may be described in, e.g., US Patent Application Publication US 2008/0188831 A1, titled MINIATURE FLEXIBLE THROMBECTOMY CATHETER (Bonnette et al.).

Among the depicted components are a manifold 12 that is attached to a proximal end of the catheter 10. The manifold 12 may include a central tubular body 16, an exhaust branch 18, and a high pressure connection branch 20 extending from the central tubular body 16. In the depicted embodiment, the proximal end of the catheter 10 is attached to the manifold 12 by the use of a Luer fitting 26 (although any other suitable connection technique may be used). The proximal end of the catheter 10 extends through a strain relief tube 28 and through the fitting 26 to communicate with the manifold 12.

The catheter 10 is shown engaged over and about a guidewire 104 where the guidewire 104 engages a lumen that opens at the distal end 37 of the catheter 10 followed by passage proximally through the catheter 10 to the location at which the guidewire 104 exits the catheter 10 as discussed in more detail herein. FIG. 1 also depicts a high pressure fluid source 106 and a high pressure fluid pump 110 connect, as shown, to the manifold 12 via the high pressure connection port 20 by connector 22 (or optionally by a direct connection) to supply high pressure saline or other suitable fluid for the catheter 10. An optional exhaust regulator 112 and a collection chamber 114 connect to the exhaust branch 18 of the manifold 12 by a fitting 19 (or optionally by direct connection) for influencing the outflow from the catheter 10. Examples of some suitable systems including high pressure fluid sources and/or exhaust collection systems may be described in, e.g., U.S. Pat. No. 6,805,684 (Bonnette et al.); U.S. Patent Application Publication No. US 2007/0129679 (Bonnette et al.); etc.

The catheter 10 is constructed of tubular components including a proximal body section 30 joined and connected to a distal body section 32 at a transition section 14. It may be preferred that proximal body section 30 and/or the distal body section 32 are constructed so as to be flexible enough to facilitate advancement of the catheter along a curved passageway such as, e.g., a blood vessel. The distal body section 32 may be, but is not necessarily, shorter than the proximal body section 30. Either or both the proximal body section 30 and the distal body section 32 may include multiple sub-sections having different external sizes. In some embodiments, however, the distal body section 32 may preferably have a uniform external size (e.g., diameter for a circular body section 32) from the distal end of the transition section 14 to at least the location of any inflow and/or outflow orifices (as described herein).

The tubular components of the catheter 10 may preferably be constructed of materials which promote pushability, torqueability, and which provide for operator feel. The proximal body section 30 may, for example, be constructed of braided polyimide, a synthetic polymeric resin, metal (e.g., stainless steel, Nitinol, etc.) or any other suitable flexible material(s), and the distal body section 32 may be constructed of Pebax, a thermoplastic elastomer, metal (e.g., stainless steel, Nitinol, etc.) or any other suitable material(s). The catheter 10 may preferably include a hydrophilic coating to enhance deliverability along the vasculature or other structure. In some embodiments, e.g., those including metallic tubing, the tubing may include spiral cuts to improve flexibility.

The external body dimensions of the proximal body section 30 and the distal body section 32 may preferably be selected such that the distal body section 32 has smaller external dimensions than the proximal body section 30 to facilitate advancement of the distal body section 32 into smaller passageways. In some embodiments, the proximal body section 30 may have an external dimension of about 4 French (Fr) as measured with reference to the French catheter scale. The distal body section 32 may include portions that have different external dimensions, whereby a proximal end of the distal body section tube 32 can, e.g., be 4 Fr size to mate with the distal end of the proximal tube 30. The more distally located portions of the distal body section 32 can be drawn and reduced or otherwise processed to reduce their external dimensions (to, e.g., a 3 Fr size) to facilitate advancement of the distal body section 32 into smaller passageways.

In some embodiments, the proximal body section 30 and the distal body section 32 are constructed of separate members that are attached to each other within the transition section 14 by any suitable technique. For example, the proximal end of the distal body section 32 may be attached to the distal end of the proximal body section 30 at a transition section 14 by drawing down the proximal end of the distal body section 32 such that it can be inserted into the distal end of the proximal body section 30. The ends of the proximal body section 30 and the distal body section 32 can then be secured together by adhesive, welding, swaging, or by any other suitable method.

In other embodiments, the proximal body section 30 and the distal body section 32 may be formed of one continuous member that may be tapered or otherwise reduced in size at one or more transition sections such that joints between separate members may not be required.

Regardless of the specific construction details, the proximal body section 30 and the distal body section 32 preferably function together as an exhaust tube for evacuation of material, e.g., macerated effluence from a thrombus or lesion site. To do so, the distal body section 32 may include one or more outflow orifices 36a-36n and one or more inflow orifices 38a-38n, the use of which is described in more detail below in connection with FIG. 7.

The catheters described herein may preferably be adapted to advancement to an internal body location using a guidewire that is threaded through a portion of the catheter. In some embodiments of thrombectomy catheters and other devices that have been adapted for delivery over a guidewire, the structures used to guide the guidewire through the catheter can, in some instances, occupy significant portions of an interior lumen of the catheter.

If the catheter is to be used for thrombectomy or other procedures in which the flow of fluid (e.g., saline) is used to remove material through a lumen in the catheter as described in, e.g., U.S. Patent Application Publication US 2008/0188831 A1, titled MINIATURE FLEXIBLE THROMBECTOMY CATHETER (Bonnette et al.), exhaust flow through the lumen can potentially be constricted by a guidewire tube that is located in the smaller section of the catheter. In some instances, obstructions in the smaller lumen, such as guidewire tubes, may result in reduced exhaust flow such that the net result is the infusion of fluid into the passageway in which the catheter is located.

The catheters described herein, although they include guidewire tubes for the guiding a guidewire within a portion of the catheter, include a truncated or shortened guidewire tube such that exhaust flow through the lumen in which the guidewire tube is located can be greater than a catheter including a guidewire tube that extend distally past a fluid jet emanator located in the distal body section of the catheter.

Figure 2:
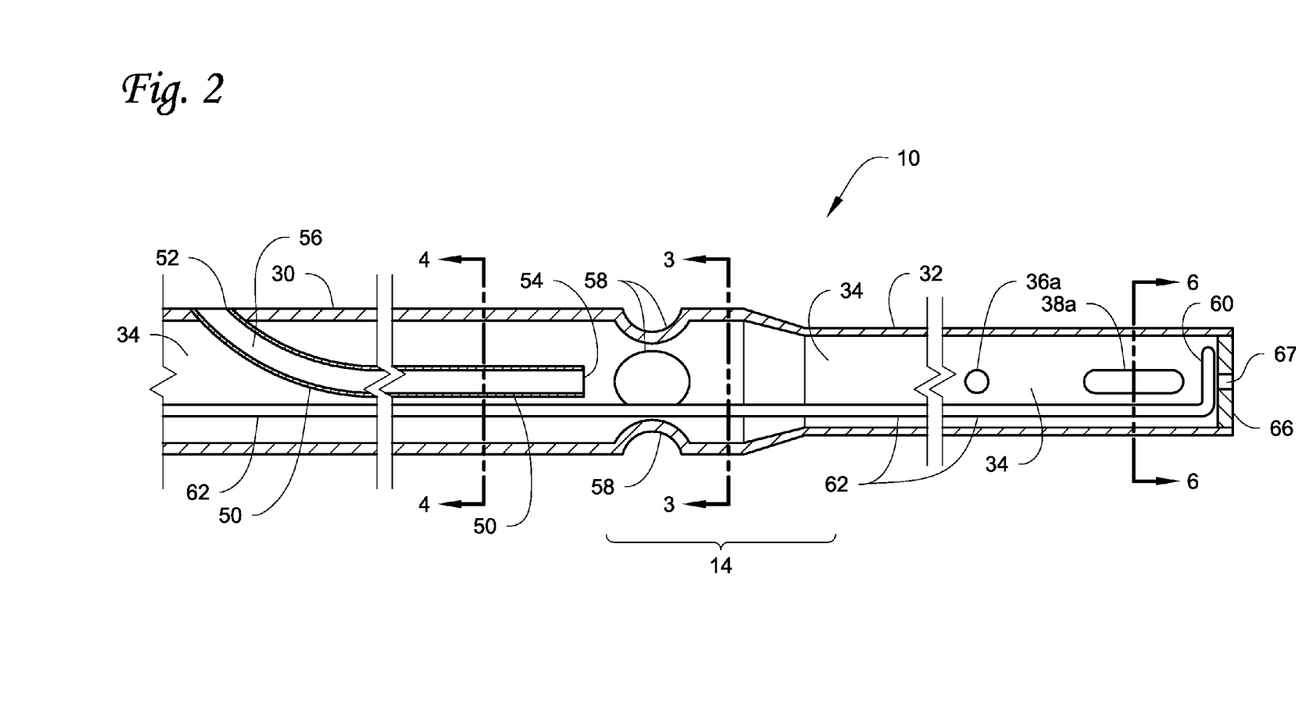
FIG. 2 is an enlarged cross-sectional view of portions of one embodiment of a catheter as described herein.

FIG. 2 is an enlarged cross-sectional view of selected portions of the catheter 10 to illustrate various features of the catheters described herein. The left-most selected portion of the catheter 10 depicted in FIG. 2 includes the proximal end 52 of the guidewire tube 50, while the right-most selected portion depicted in FIG. 2 includes a fluid jet emanator 60 and attached fluid delivery tube 62 that extends in the proximal direction through the catheter 10.

Figure 3:
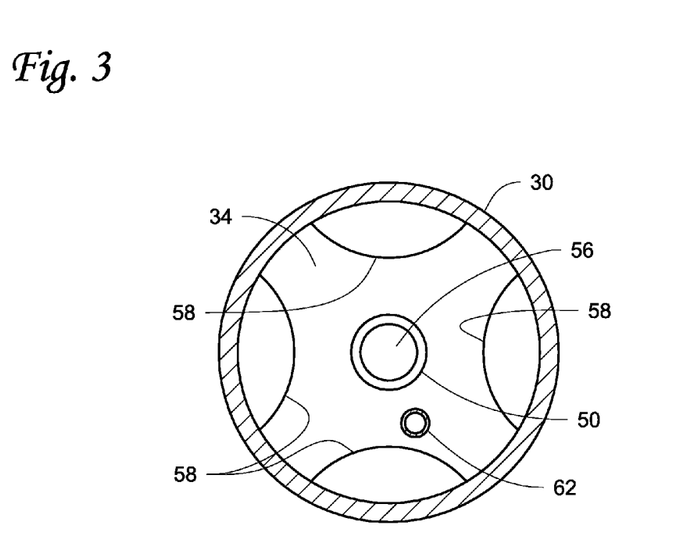
FIG. 3 is a cross-sectional view the catheter depicted in FIG. 2 taken along line 3-3 in FIG. 2.

The center portion of the catheter 10 that is depicted in FIG. 2 includes a transition section 14 between the proximal body section 30 and the distal body section 32, along with the distal end 54 of the guidewire tube 50. FIG. 3 is a cross-sectional view taken within the center portion of FIG. 2 and includes the guidewire tube 50. The view of FIG. 3 shows the distal port at the distal end of the guidewire tube 50 that opens into the lumen 56 that extends through the guidewire tube 50 to the proximal end 52 of the guidewire tube 50 (where the lumen 56 preferably opens to the exterior of the catheter 10 at a proximal port).

FIGS. 2 and 3 also depict the optional guide structures 58 that may be provided to assist in directing the proximal end of a guidewire (not shown) into the lumen 56 of the guidewire tube 50. In the depicted embodiment, the guide structures 58 may take the form of protrusions that may, for example, be formed as dents in the tubing of the proximal body section 30. Although four guide structures 58 are depicted in FIGS. 2 and 3, the catheters described herein may include any suitable number of the guide structures, i.e., the catheters may include one, two, three, four, or more guide structures. It may be preferred that the distal end 54 of the guidewire tube 50 be located proximally of the guide structures 58 as depicted in FIG. 2, although in some embodiments the guide structures 58 may be located around the distal end 54 of the guidewire tube 50.

Regardless of the exact nature of any guide structures used to help direct a guidewire into the guidewire tube 50, a balance will need to be made between the ability of the guide structures to accomplish their directing function and their impact on the fluid flow through the exhaust lumen 34.

Figure 4:
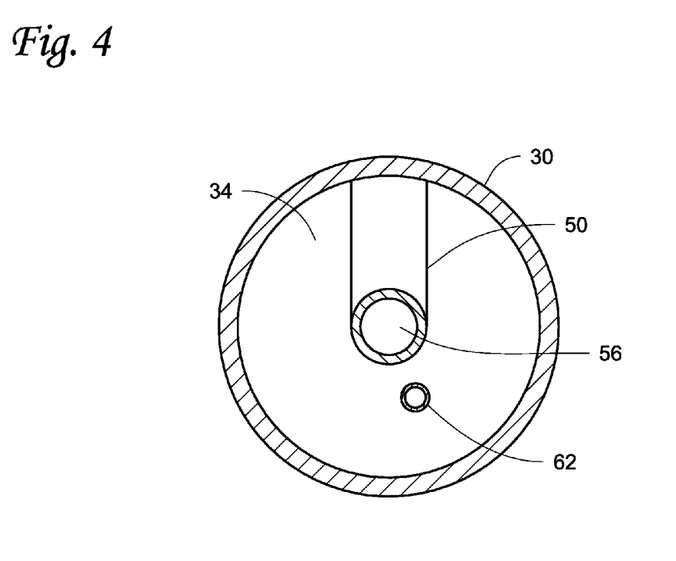
FIG. 4 is a cross-sectional view the catheter depicted in FIG. 2 taken along line 4-4 in FIG. 2.

As seen in the combination of the center portion and the left-most portion of FIG. 2 and the cross-sectional view of FIG. 4, the guidewire tube 50 may preferably terminate at its proximal end 52 in an opening made through a sidewall of the proximal body section 30 of the catheter 10. In the depicted embodiment, the guidewire tube 50 may include a bend to achieve that function, with a bend being depicted in the left-most portion of the FIG. 2. In other embodiments, the guidewire tube 50 may be straight or nearly straight and may exit the proximal body section of the guidewire tube through a structure or structures as described in connection with FIGS. 15-17 of US Patent Application Publication US 2008/0188831 A1, titled MINIATURE FLEXIBLE THROMBECTOMY CATHETER (Bonnette et al.). Although the guidewire tube is depicted as a homogeneous and unitary element, it may alternatively be constructed as a composite of multiple components so long as the components define a lumen capable of guiding a guidewire through the tube from its distal end to its proximal end.

As depicted in FIGS. 2-3, the distal end 54 of the guidewire tube 50 may be generally centered within the exhaust lumen 34. In some embodiments, however, the distal end 54 (and its corresponding distal port into the guidewire lumen 56) may not be centered within the exhaust lumen 34. If the distal end of the guidewire tube 50 is not centered, any protrusions or other guide structures that may be provided to direct a guidewire into the guidewire tube 50 may also be adjusted accordingly.

As discussed herein, the guidewire tube 50 is located within only a portion of the catheter 10. Generally speaking, the guidewire tube 50 may be described as having a distal end that terminates at a location that is proximal from the fluid jet emanator 60. In some embodiments, the distal end 54 of the guidewire tube 50 may be located between the proximal end of the distal body section 32 (where the proximal end is, e.g., located on the distal side of the transition section 14) and the proximal end 52 of the guidewire tube 50.

As depicted in FIG. 2, the proximal end 52 of the guidewire tube 50 may preferably be located in the proximal body section 30 of the catheter 10. In some embodiments, the distal end 54 of such a guidewire tube 50 may preferably be located between the proximal end of the distal body section 32 (where the proximal end is, e.g., located on the distal side of the transition section 14) and the proximal end 52 of the guidewire tube 50. Depending on the nature and construction of the transition section 14, the distal end 54 of the guidewire tube 50 may be located within the portion of the catheter 10 that is occupied by the transition section 14 between the proximal body section 30 and the distal body section 32.

In still other embodiments, the proximal end 52 of the guidewire tube 50 may be described as being located in the proximal body section 30 of the catheter 10 between the proximal end of the catheter 10 and the transition section 14 between the proximal body section 30 and the distal body section 32.

Among the features depicted in the various portions of FIG. 2 is the exhaust lumen 34 that extends through all of the portions of the catheter 10. The exhaust lumen 34 has a proximal cross-sectional area within the proximal body section 30 (on the proximal side of the transition section 14) that is larger than the cross-sectional area of the exhaust lumen 34 in the distal body section 32 (on the distal side of the transition section 14). The exhaust lumen 34 may preferably extend to the proximal end of the catheter 10 where is can be connected to other components (e.g., the manifold 12) to remove material as discussed in, e.g., U.S. Patent Application Publication US 2008/0188831 A1, titled MINIATURE FLEXIBLE THROMBECTOMY CATHETER (Bonnette et al.).

Another feature depicted in the various portions of FIG. 2 is the fluid delivery tube 62 that is attached to the fluid jet emanator 60 depicted in the right-most portion of FIG. 2. The fluid delivery tube 62 preferably extends through the exhaust lumen 34 in at least a portion of both the proximal body section 30 and the distal body section 32. Although not depicted in FIG. 2, the fluid delivery tube 62 may be constructed of multiple components as discussed in, e.g., U.S. Patent Application Publication US 2008/0188831 A1, titled MINIATURE FLEXIBLE THROMBECTOMY CATHETER (Bonnette et al.). Other examples of potentially suitable fluid jet emanators and fluid delivery tubes used to deliver fluid to them may be described in. e.g., U.S. Pat. No. 6,875,193 (Bonnette et al.); U.S. Pat. No. 6,755,803 (Le et al.); U.S. Patent Application Publication US 2006/0064123 A1 (Bonnette et al.); etc.

Yet another feature depicted in FIG. 2 is an outflow orifice 36a and an inflow orifice 38a, at least one of and/or both of which may, in some embodiments, be provided in the distal body section 32 of the catheter. The functions of the outflow orifice 36a and the inflow orifice 38a will be described in more detail herein with respect to FIG. 7 herein.

Another optional feature that may be provided in connection with the catheters described herein is a funnel structure that may be attached to the guidewire tube 150 itself to direct a guidewire into the distal end of the guidewire tube 150. One potentially suitable example of a funnel structure is depicted in connection with FIG. 5 is in the form of a flared distal end 154 on the guidewire tube 150.

In place of or in addition to a funnel structure on the end of the guidewire tube, other structures such as cages, struts, etc. that extend outwardly and serve to direct a guidewire into the guidewire tube may also be used. It may be beneficial if such structures include openings, notches, etc. such that fluid can flow through the guiding structure used.

Figure 5:
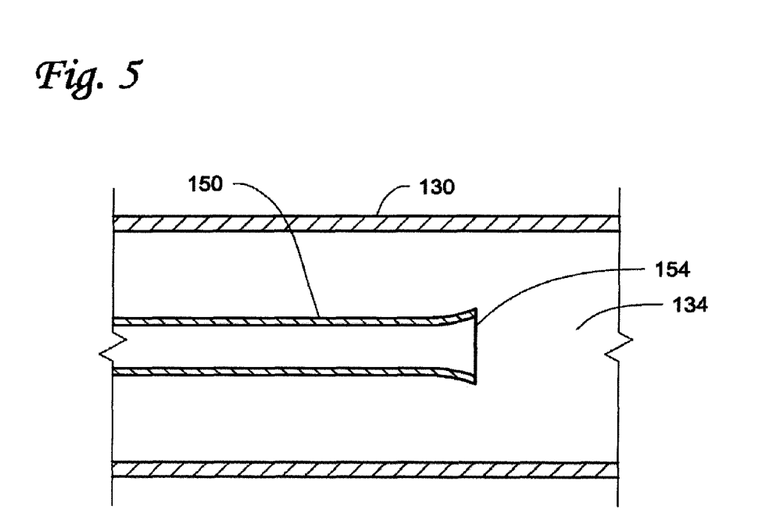
FIG. 5 depicts a guidewire tube having a flared distal end.

Although no guide structures are depicted in the exhaust lumen 134 defined by the body section 130 depicted in FIG. 5, guide structures (such as, e.g., the protrusions depicted in FIG. 3) may be provided in addition to a funnel structure to further assist in directing a guidewire into the guidewire tube.

Figure 6:
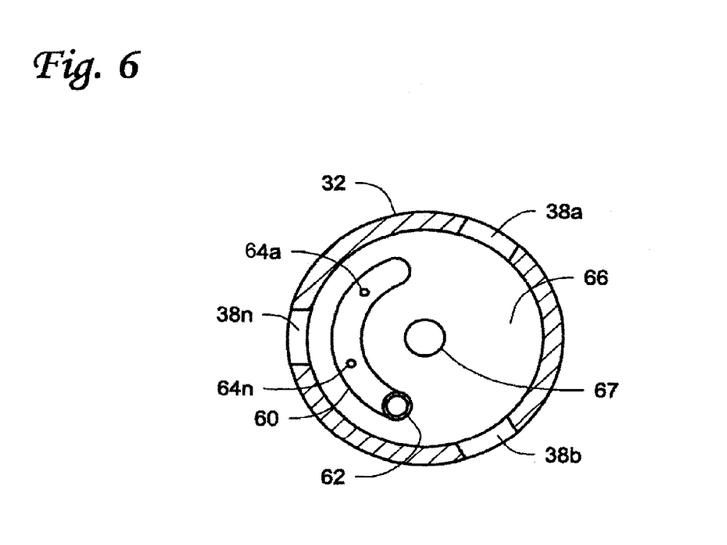
FIG. 6 is a cross-sectional view the catheter depicted in FIG. 2 taken along line 6-6 in FIG. 2.

FIG. 6 is an enlarged cross-sectional view taken along line 6-6 in FIG. 2 towards the distal end of the catheter 10 depicting the components of the fluid jet emanator 60 that are located within the distal body section 32 of the catheter 10. Among the features depicted in FIG. 6 are the fluid delivery tube 62. The depicted fluid jet emanator 60 includes proximally directed jet orifices 64a-64n located on the proximal side of the fluid jet emanator 60 for the creation of a cross stream jet incorporating the outflow orifices 36a-36n (see, e.g., FIGS. 1 and 7) and inflow orifices 38a-38n of the catheter 10. The outflow orifices 36a-36n, as well as the inflow orifices 38a-38n, may be spaced around the catheter at, e.g., 120.degree. intervals or other suitable intervals.

Although the fluid jet emanator 60 is in the form of an arcuate foreshortened loop which at least partially defines a guidewire orifice within the lumen 34 that allows the passage of a guidewire through the loop and the lumen 34 in the proximal direction. The fluid jet emanators used in connection with the catheters described herein may take a variety of other forms (i.e., they are not limited to the arcuate loop depicted in FIG. 6), for example, the fluid jet emanators may be in the form of a larger loop (e.g., a 350+ degree loop) or other bodies/structures that do not include arcuate tubing (such as the fluid jet emanators described in, e.g., U.S. Patent Application Publication US 2006/0064123 A1 (Bonnette et al.).

The fluid jet emanator 60 depicted in FIGS. 2 and 6 may rest against or otherwise be supported by a support ring 66 located on the distal side of the fluid jet emanator 60. The support ring 66 may preferably include a guidewire orifice 67 to allow a guidewire that is inserted into the distal end of the catheter 10 to pass through the support ring 66. The fluid jet emanator 60 also preferably allows the guidewire to be advanced in the proximal direction towards the guidewire tube as discussed herein. If a fluid jet emanator is used in catheters such as those described herein that is not in the form an arcuate tube, then the fluid jet emanator itself may include a guidewire orifice (see, e.g., passageway 104 in FIGS. 13-14 of U.S. Patent Application Publication US 2006/0064123 A1 (Bonnette et al.)).

Figure 7:
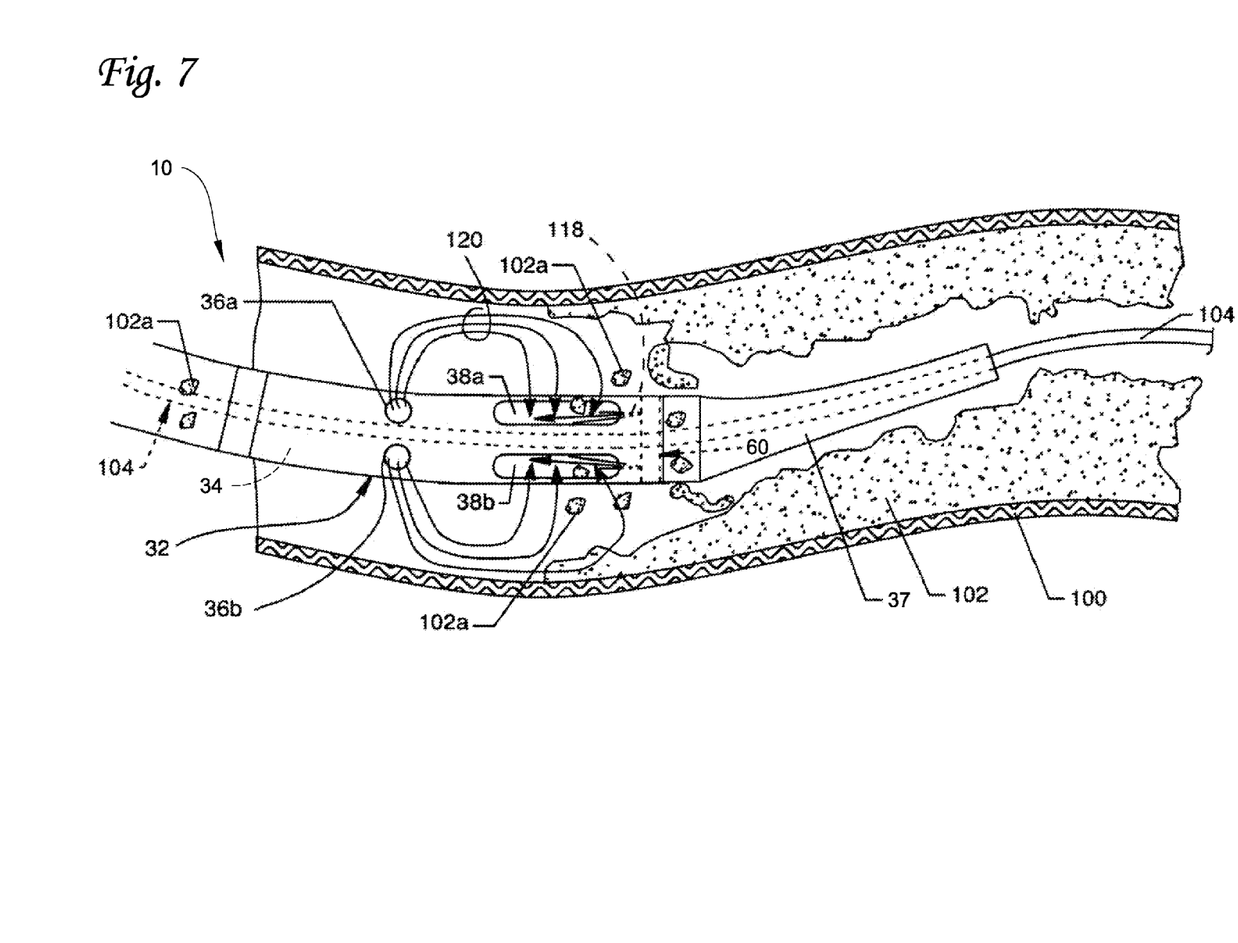
FIG. 7 depicts one embodiment of a catheter described herein in use within a blood vessel.

FIGS. 1 and 7 can be used to describe one mode of operation of one catheter as described herein, where FIG. 1 illustrates the catheter 10 connected to the various components of the system, and where FIG. 7 illustrates a side view of the distal region of the catheter 10 in the performance of a method of using the catheter 10 within a small blood vessel 100 (shown in cross section) at a site of a thrombotic deposit or lesion 102.

In FIG. 1, the rapid exchange catheter 10 is shown engaged over and about a guidewire 104 where the guidewire 104 (previously located in the blood vessel 100 of FIG. 7) first engages the catheter 10 at its optional flexible distal tip 37 followed by exiting from the guidewire tube (see, e.g., guidewire tube 50 in FIG. 2). FIG. 7 is a side view of the distal portion of the catheter 10 in the performance of one illustrative method of use. Generally, the guidewire 104 is deployed in a blood vessel 100 (or other lumen) before introducing the catheter 10. Any suitable guidewire may be used, e.g., a normal guidewire, a filter guidewire, a balloon occlusion guidewire, etc.

The catheter 10, with its components (e.g., fluid delivery tube, fluid jet emanator, etc.) is advanced over and along the guidewire 104 which is aligned within the blood vessel 100 for, in the depicted embodiment, the purpose of debris/thrombus/lesion removal and maneuvered into an appropriate position for treatment. In some embodiments, other therapies/treatments may be provided, e.g., drug infusion, etc.

In some embodiments, a guide catheter or sheath can be used in connection with catheter 10 to provide assistance in placing the catheter 10 within the desired location of the blood vessel 100 in order that the tapered tip 37 of the catheter 10 can be advanced through the thrombus or lesions 102 to position the fluid jet emanator in very close proximity to the thrombus or lesions 102. Although depicted in one location in FIG. 7, the catheter 10 may be moved proximally or distally during the procedure to maximize the effect of the catheter system. Further interventions can be executed as normal over the remaining guidewire or guidewire device.

FIG. 7 is a side view, in partial cross section, of the catheter 10 in the performance of one embodiment of a method as described herein. As discussed, the catheter 10 is engaged over and about the guidewire 104 wherein the guidewire 104 (which may have been previously inserted into the body lumen, e.g., a vein, artery, etc.) can first slideably pass through a passageway provided through the optional tapered flexible tip 37. The guidewire 104 enters the catheter 10, where it is located within the exhaust lumen 34 after passing through the fluid jet emanator located within the catheter 10 (see, e.g., FIGS. 2 and 6 for views of some embodiments of fluid jet emanators that may be used in catheter 10). The guidewire 104 is directed in the proximal direction through the exhaust lumen 34 past the inflow orifices 38a-38n and the outflow orifices 36a-36n.

The pressurized fluid (e.g., saline or other suitable fluids such as drugs, etc.) delivered to the fluid jet emanator in the catheter 10, in combination with the outflow orifices 36a-36n and inflow orifices 38a-38n, preferably produces non-hemolyzing cross stream jets 120 of saline or other suitable fluids which emanate from the outflow orifices 36a-36n to accomplish thrombectomy functions, as described herein. Cross stream jets 120 with characteristics that fall short of hemolysis by, e.g., controlling the input fluid pressure at the high pressure fluid pump 110 and/or by controlling the exhaust rate at the exhaust regulator 112, whereby the exhaust regulator 112 may be operated to, e.g., provide a negative pressure for effluent aspiration.

The cross stream jets 120 emanating from the outflow orifices 36a-36n provide for the fluid jet impingement of the deposits of thrombus or lesions 102 on the inner wall of the blood vessel 100 adjacent to or in close proximity to the orifices 36a-36n in order to impinge, ablate and loosen deposits of thrombus or lesions 102, whereby such thrombus or lesion particulate and fluids can be entrained through one or more inflow orifices 38a-38n by aspiration into the exhaust lumen 34 and removed proximally through the exhaust lumen 34 using, e.g., an exhaust regulator 112. In some embodiments, manual aspiration methods could potentially be used as well. Although multiple inflow orifices 38a-38n are found in the depicted embodiment, as few as one inflow orifice may be provided in some embodiments.

In some embodiments, drugs for treatment or for lysing of the thrombus or lesions 102 can also be delivered via the outflow orifices 36a-36n to, e.g., soften the deposits of thrombus or lesions 102 in the region of the blood vessel 100 adjacent to or in close proximity to the outflow orifices 36a-36n. Any such drugs may, e.g., be delivered through the fluid delivery tube delivering fluid to the fluid jet emanator, through a separate lumen, using a different fluid delivery device (e.g., catheter, etc.).

As depicted in FIG. 7, multiple high velocity fluid jet streams 118 of a suitable fluid (e.g., saline, etc.) are shown being emitted in a proximal direction from the fluid jet emanator 60 to form the cross-stream jets 120 that impinge upon and carry away thrombotic deposits or lesions 102 as particles 102a. Other fluid jet emanators of appropriate size and/or configuration can be incorporated within the distal portion of the distal body section 32 as an alternative to the fluid jet emanator 60 illustrated in this figure to emanate or emit one or more fluid jet streams to accomplish the same purpose as that described for the fluid jet emanator 60.

In the depicted embodiment, the high velocity fluid jet streams 118 pass outwardly through the outflow orifices 36a-36n in a radial direction, thereby creating cross stream jets 120 (lower velocity jets) directed outwardly toward the wall of the blood vessel 100 and are influenced by the low pressure at the inflow orifices 38a-38n to cause the cross stream jets 120 to flow circumferentially and distally to impinge on, provide drag forces on, and break up thrombotic deposits or lesions 102 and to, by entrainment, urge and carry along the particles 102a of thrombotic deposits or lesions 102 through the inflow orifices 38a-38n, a relatively low pressure region, into the high velocity fluid jet streams 118 where the thrombus is further macerated into microscopic particles, and then into the exhaust lumen 34 of the distal body section 32 (see, e.g., FIG. 2).

A certain portion of this macerated debris which is mixed with fresh fluid provided through the fluid jet emanator is removed through the exhaust lumen 34 and a certain portion flows back out the outflow orifices 36a-36n and recirculates to break up more debris which is returned to the inflow orifices 38a-38n. In this way, more fluid flow may circulate through the system than is injected through the jet emanator. For purposes of illustration and example, in some embodiments three to ten times more flow circulates through the system than is delivered by the jet emanator. The entrainment through the inflow orifices 38a-38n is based on entrainment by the high velocity fluid jet streams 118. The outflow is driven by internal pressure which is created by the high velocity fluid jet streams 118 and the fluid entrained through the inflow orifices 38a-38n.

Enhanced clot removal may be attainable because of the recirculation pattern established between outflow and inflow orifices 36a-36n and 38a-38n, which may create a flow field that increases drag force on wall-adhered thrombus. Since the entrained thrombus is macerated into microscopic particles 102a, those particles that exit the outflow orifices 36a-36n are preferably not of sufficient size to significantly block the distal circulation, and will often be re-entrained into the inflow orifices 38a-38n at a high rate. In a no-flow situation or when flow is stopped with another device, such as an occlusive balloon, material can be recirculated and rediluted until all that remains is saline and all particles are removed.

The sizing of the various components used in connection with the systems and methods described herein may vary based on a number of factors such as, e.g., size of the catheter, materials to be removed using the catheter, fluid flow rates desired, etc. In general, however, jet orifices in the fluid jet emanators can range in size, e.g., from 0.001 inch to 0.040 inch for emanation of saline or other suitable fluid therefrom in a velocity range of 1 to 250 m/s. By sizing the jet orifices and adjusting the high pressure fluid pump, the velocity and strength of the cross stream fluid flow can be controlled. The general operating pressures of the catheter system may, for example, range from 50 psi to 20,000 psi. The fluid delivery tubes may, in one embodiment, be circular tubes with an outside diameter of about 0.018 inch and in inside diameter of about 0.012 inch over a proximal portion, and an outside diameter of about 0.011 inch and an inside diameter of about 0.008 inch over an intermediate portion, and an outside diameter of about 0.007 inch and an inside diameter of about 0.004 inch over a distal portion, although other tube profiles and/or dimensions may be used.

The catheter body sections may have a variety of different tubular profiles and/or dimensions, although in some embodiments, the distal body sections attached to the distal ends of the transition sections may be circular in profile and have an outside diameter of about 0.039 inch, (corresponding to an external size of 3 French), and an inside diameter of about 0.033 inch. The proximal body sections attached to the proximal ends of the transition sections may have a circular profile with an outside diameter of about 0.052 inch (corresponding to an external size of 4 French), and an inside diameter of about 0.046 inch.

The guidewire tubes may also vary in size, although in some embodiments, the guidewire tube may be provided in the form of a circular tube that has in outside diameter of about 0.0205 inch and an inside diameter of about 0.0165 inch. Other guidewire tubes having different profiles and/or dimensions may be used. The length of the guidewire tube may vary depending on the selected locations for its proximal and distal ends.

Figure 8:
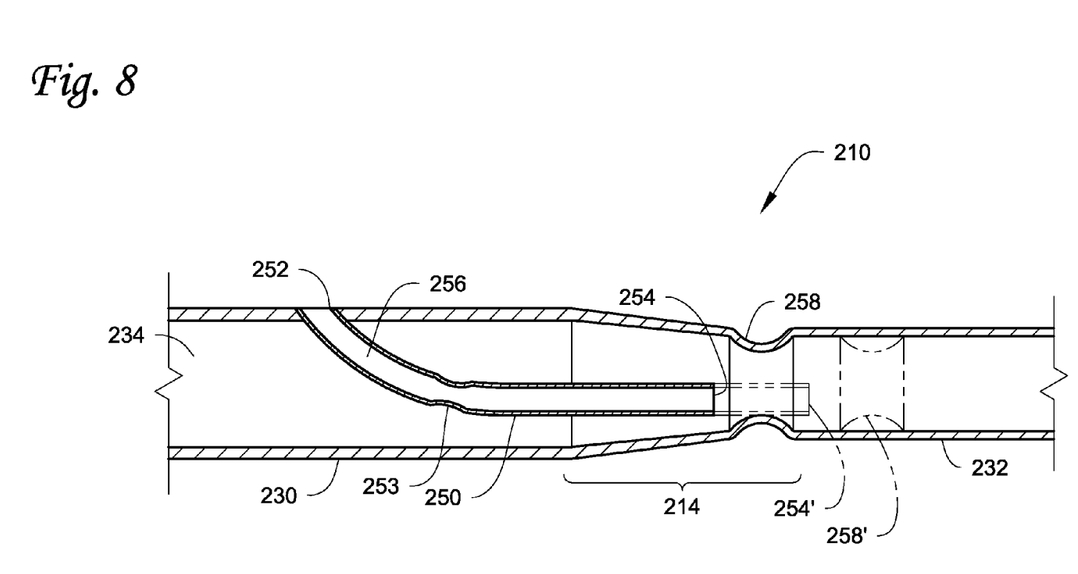
FIG. 8 is an enlarged cross-sectional view of portions of another embodiment of a catheter as described herein.

Another embodiment of a catheter that may be used as described herein is depicted in the cross-sectional view of FIG. 8 (which is similar in many respects to the view seen in FIG. 2). One difference between the catheter 10 of FIG. 2 and the catheter 210 of FIG. 8 is that the transition section 214 of catheter 210 is longer as compared to the transition section 14 seen in FIG. 2. The transition section 214 is still located between a proximal body section 230 and a distal body section 232. In one embodiment, the longer transition section may have a length of about 2.5 centimeters (cm), although in some embodiments, the guidewire tube may have a length of about 1 cm or longer, 2 cm or longer, etc.

In the embodiment depicted in FIG. 8, the guide structure 258 is in the form of a annular protrusion that extends into the exhaust lumen 234 (in contrast to the discrete protrusions 58 described in connection with catheter 10). The annular protrusion 258 may extend completely around the perimeter of the catheter 210 or it may extend only partially around the perimeter.

Although the annular protrusion 258 is located in the transition section 214, it may alternatively be located more distally or proximally. The protrusion 258' depicted in broken lines in FIG. 8 is an example of a more distally located protrusion. The protrusion 258' is located distally from the transition section 214 and, as a result, can be described as being located in the distal body section 232 of the catheter 210. In such an embodiment, the guidewire tube 250 may also extend further such that its distal end 254' (depicted in broken lines in FIG. 8) is located distally from the proximal end of the distal body section 232 (i.e., the distal end 254' of the guidewire tube 250 is located in the distal body section 232 of the catheter 210). In still other embodiments, any protrusions and the distal end of the guidewire tubes may be located entirely within the proximal body section 230 such that neither protrusions or the guidewire tube are located in the transition section or the distal body section.

Another optional feature in the embodiment depicted in FIG. 8 is that the guidewire tube 250 may also include a restriction 253 located between its proximal end 252 and its distal end 254. The restriction 253 preferably reduces the size of the lumen 256 at a location proximal from the distal end 254 of the guidewire tube 250. Such a restriction 253 may serve to reduce flow through the guidewire tube 250 as liquid and other materials flow in the proximal direction through the exhaust lumen 234 while not unduly restricting the ability of a guidewire to enter the distal end 254 of the guidewire lumen 250.

The restriction 253 may take any of a number of forms. Some potentially suitable examples may include, but are not limited to, one or more protrusions into the lumen of the guidewire tube (similar to, e.g., protrusions 58 and 258 described herein), a necked-down section, a plug located in the guidewire tube 250 (with the plug retaining a passageway therethrough to allow a guidewire to pass through the restriction), etc. If a plug is used, it may be constructed of any suitable material(s), e.g., silicone, urethane, metal, etc.

Figure 9:
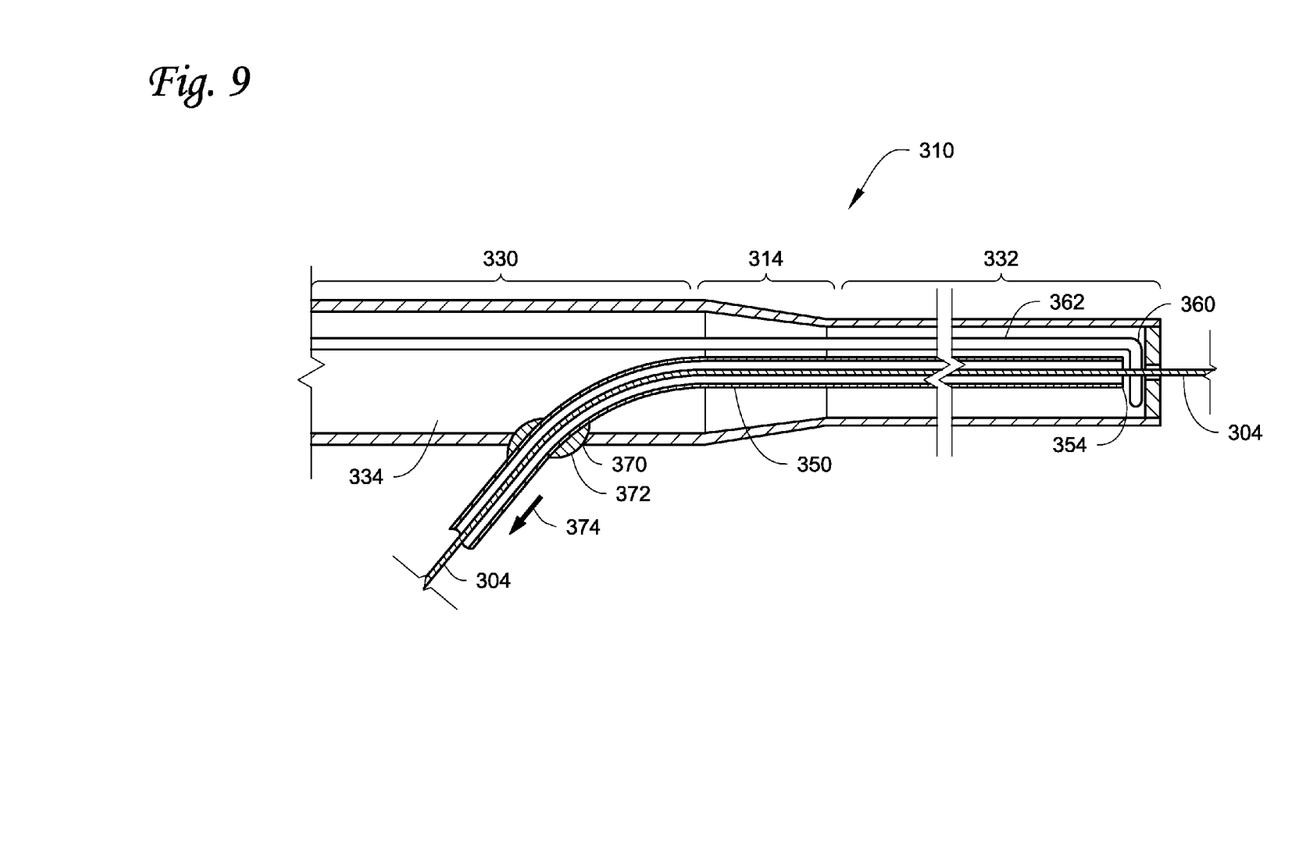
FIG. 9 is an enlarged cross-sectional view of portions of another embodiment of a catheter as described herein.

Another embodiment of a catheter 310 is depicted in FIG. 9 and includes a proximal body section 330 connected to a distal body section 332 through a transition section 314. A fluid jet emanator 360 is provided and attached to a fluid delivery tube 362 that extends proximally through the exhaust lumen 334 in the catheter 310.

Also provided in the embodiment depicted in FIG. 9 is a guidewire tube 350 that extends into the exhaust lumen 334 through a guidewire tube port 370. The guidewire tube 350 may preferably extend through the exhaust lumen 334 such that its distal end 354 is located on the proximal side of the fluid jet emanator 360.

The guidewire tube 350 in the embodiment depicted in FIG. 9 is preferably removable from the exhaust lumen 334 by withdrawing it through the port 370 in the direction of arrow 374. It may be preferred to use a guidewire tube with smaller dimensions than the guidewire tubes that remain in place. For example, a removable guidewire tube may have a circular profile with an outside diameter of about 0.0205 inch and an inside diameter of about 0.0155 inch or, in another embodiment, outside diameter of about 0.019 inch and an inside diameter of about 0.0155 inch. Other guidewire tubes having different profiles and/or dimensions may be used.

The guidewire tube port 370 preferably includes a seal 372 such that, upon removal of the guidewire tube 350, the port 370 can be substantially closed. If the guidewire 304 is left in place such that it extends through the port 370 after removal of the guidewire tube 350, then the seal 372 may preferably seal around the guidewire 304. The seal 372 may not necessarily need to form a fluid-tight seal in or over the port 370. In other words, the seal 372 may only serve to substantially close the port 370 after removal of the guidewire tube 350. The seal 370 may take a wide variety of forms, although it may preferably be formed of a flexible, resilient material, e.g., silicone, urethane, etc. It may be in the form of an O-ring, one or more flaps, etc.

By removing the guidewire tube 350, flow through the exhaust lumen 334 may be enhanced and, in addition, placement of the distal end 354 of the guidewire tube 350 adjacent the fluid jet emanator 360, advancement of the guidewire 304 into the guidewire tube 350 may be improved and/or simplified.

The complete disclosure of the patents, patent documents, and publications cited in the Background, the Detailed Description of Exemplary Embodiments, and elsewhere herein are incorporated by reference in their entirety as if each were individually incorporated.

Exemplary embodiments of catheters and methods have been discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below and equivalents thereof.

The invention claimed is:

1. A catheter comprising:
   an elongated catheter body comprising a proximal end and a distal end, wherein a longitudinal axis extends between the proximal end and the distal end, and wherein the catheter body comprises a proximal body section and a distal body section, wherein a distal end of the proximal body section is attached to a proximal end of the distal body section at a transition section of the catheter body;
   an exhaust lumen located within the catheter body, the exhaust lumen being aligned with the longitudinal axis, wherein the exhaust lumen comprises a proximal cross-sectional area on a proximal side of the transition section that is larger than a distal cross-sectional area of the exhaust lumen on a distal side of the transition section;
   a fluid jet emanator located in the distal body section;
   a fluid delivery tube attached to the fluid jet emanator, the fluid delivery tube extending through at least a portion of the proximal body section, wherein the fluid delivery tube passes from the proximal body section into the distal body section through the transition section; and
   a guidewire tube located within only a portion of the catheter body, wherein the guidewire tube comprises a proximal end and a distal end, wherein the guidewire tube comprises a guidewire lumen extending from a proximal port at the proximal end of the guidewire tube to a distal port at the distal end of the guidewire tube, and wherein the distal port of the guidewire lumen opens into the exhaust lumen at a location proximal from the fluid jet emanator.

2. A catheter according to claim 1, wherein the distal end of the guidewire tube is located between the proximal end of the distal body section and the proximal end of the guidewire tube.

3. A catheter according to claim 1, wherein the proximal end of the guidewire tube is located in the proximal body section of the catheter body and wherein the distal end of the guidewire tube is located between the proximal end of the distal body section and the proximal end of the guidewire tube.

4. A catheter according to claim 1, wherein the proximal end of the guidewire tube is located in the proximal body section of the catheter body.

5. A catheter according to claim 1, wherein the proximal end of the guidewire tube is located in the proximal body section of the catheter body and the distal end of the guidewire tube is located in the transition section.

6. A catheter according to claim 1, further comprising one or more protrusions extending into the exhaust lumen in a direction transverse to the longitudinal axis.

7. A catheter according to claim 1, wherein the distal end of the guidewire lumen is flared such that the distal port of the guidewire lumen is enlarged in a direction transverse to the longitudinal axis.

8. A catheter according to claim 1, wherein the fluid jet emanator comprises a guidewire orifice, such that a guidewire directed into the exhaust lumen from the distal end of the catheter body and advanced proximally toward the proximal end of the catheter body passes through the guidewire orifice before entering the distal port of the guidewire lumen.

9. A catheter according to claim 1, wherein the catheter body comprises a guidewire tube port that comprises a seal, wherein the guidewire tube extends through the guidewire tube port and into the exhaust lumen, and wherein the seal restricts fluid flow out of the exhaust lumen through the guidewire port around the guidewire tube.

10. A catheter according to claim 9, wherein the guidewire tube is removable from the guidewire tube port and wherein the seal comprises a seal orifice that seals around a guidewire extending through the guidewire tube port after removal of the guidewire tube from the guidewire tube port.

11. A catheter according to claim 9, wherein the fluid jet emanator comprises a guidewire orifice, such that a guidewire directed into the exhaust lumen from the distal end of the catheter body and advanced proximally toward the proximal end of the catheter body passes through the guidewire orifice before entering the distal port of the guidewire lumen.

12. A catheter according to claim 9, wherein the distal end of the guidewire tube is located between the proximal end of the distal body section and the fluid jet emanator.

13. A catheter according to claim 9, wherein the proximal end of the guidewire tube is located in the proximal body section of the catheter body.

14. A catheter according to claim 9, wherein the proximal end of the guidewire tube is located in the proximal body section of the catheter body and wherein the distal end of the guidewire tube is located in the transition section.

15. A catheter according to claim 1, wherein the catheter body further comprises at least one outflow orifice and at least one inflow orifice, wherein at least a portion of pressurized fluid delivered to the fluid jet emanator through the fluid delivery tube emanates from the catheter body through the at least one outflow orifice, and wherein at least a portion of the fluid that emanates from the catheter body through the at least one outflow orifice re-enters the catheter body through the at least one inflow orifice, and further wherein the at least one inflow orifice is located in the distal body section of the catheter body.

* * * * *

UNITED STATES PATENT AND TRADEMARK OFFICE
CERTIFICATE OF CORRECTION

| | | |
|---|---|---|
| PATENT NO. | : 8,353,858 B2 | Page 1 of 1 |
| APPLICATION NO. | : 12/793121 | |
| DATED | : January 15, 2013 | |
| INVENTOR(S) | : Kozak et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 347 days.

Signed and Sealed this
Fifth Day of November, 2013

Teresa Stanek Rea
*Deputy Director of the United States Patent and Trademark Office*